United States Patent [19]

Lebesgue et al.

[11] Patent Number: 4,632,692
[45] Date of Patent: Dec. 30, 1986

[54] PROCESS AND INSTALLATION FOR SIMULTANEOUSLY PRODUCING COMPOST AND BIOGAS FROM ORGANIC WASTE

[75] Inventors: Yves Lebesgue, Vigny; Alexandru Zeana, Creteil, both of France

[73] Assignee: Societe Multibio, France

[21] Appl. No.: 644,193

[22] Filed: Aug. 24, 1984

[51] Int. Cl.[4] .................................................. C05F 7/04
[52] U.S. Cl. .......................................... 71/10; 210/630
[58] Field of Search ................. 71/8, 10; 210/603, 630

[56] References Cited

U.S. PATENT DOCUMENTS 4,198,211 4/1980 Shattock ........................... 210/603 X
4,350,588 9/1982 Tsubota ............................ 210/603 X Primary Examiner—Ferris H. Lander
Attorney, Agent, or Firm—Scully, Scott, Murphy & Presser

[57] ABSTRACT

The invention relates to a process for the simultaneous treatment of solid or semi-solid organic waste and liquid organic waste with a view to the simultaneous production of compost and biogas.

According to this process, said liquid organic waste is subjected to a liquid-solid separation, the liquid phase from this separation is subjected to anaerobic fermentation in at least one closed digester, the solid phase from said liquid-solid separation is mixed with said solid or semi-solid organic waste, the resulting mixture is subjected to aerobic fermentation at the periphery of said digester and in contact therewith and mud, clarified liquid and gas are respectively discharged from said digester whereas compost from the aerobic fermentation of said solid or semisolid waste is recovered at the periphery of said digester.

10 Claims, 5 Drawing Figures

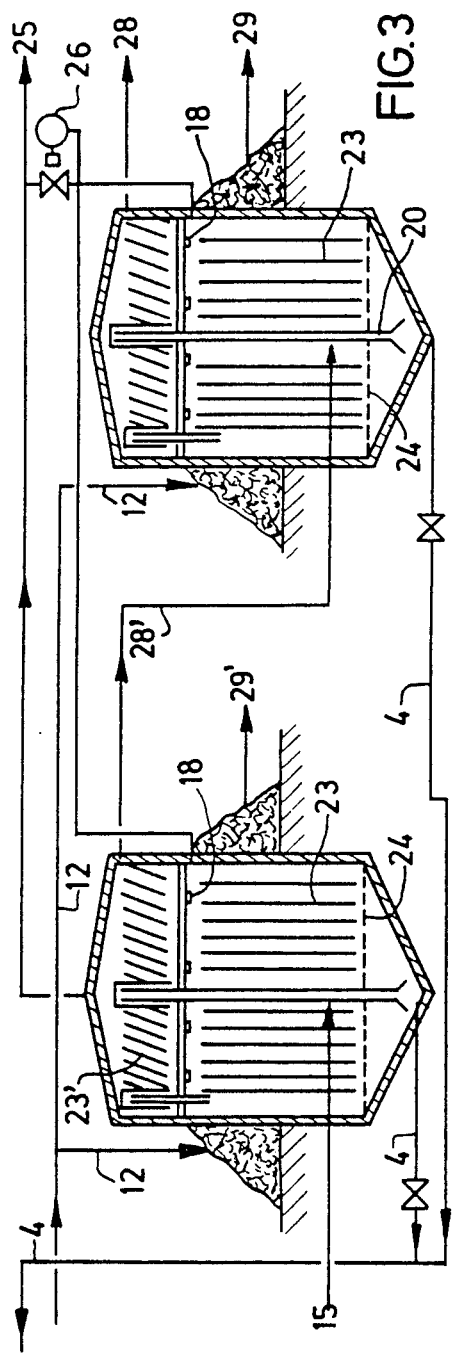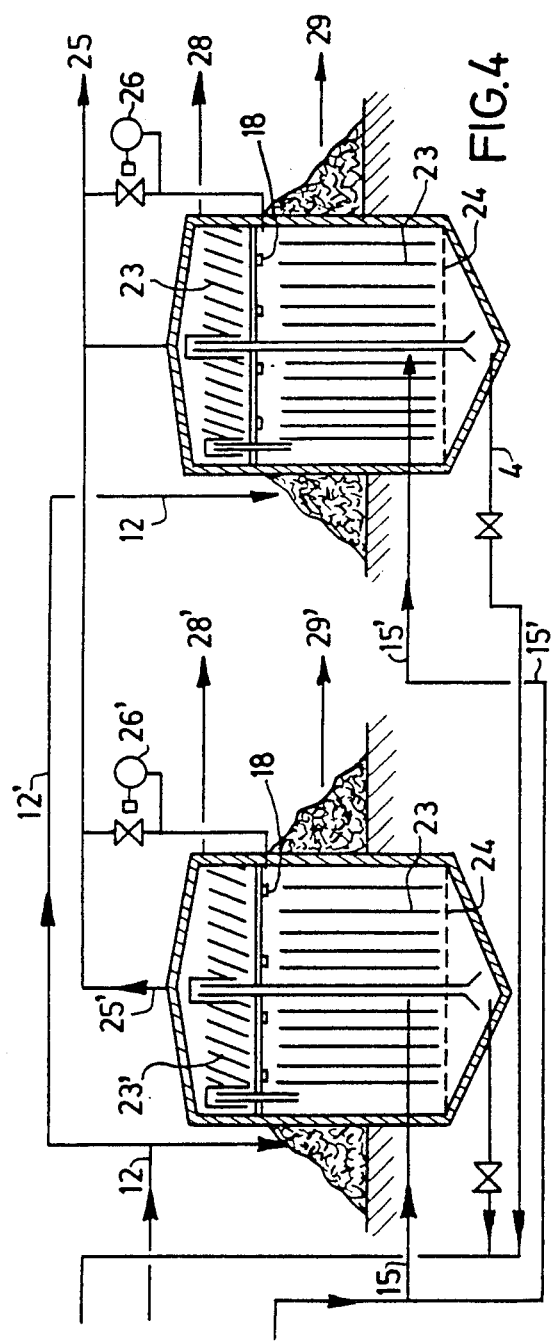

PROCESS AND INSTALLATION FOR SIMULTANEOUSLY PRODUCING COMPOST AND BIOGAS FROM ORGANIC WASTE

BACKGROUND OF THE INVENTION

1. Field of the Invention

The present invention concerns the valuable use made of liquid and/or solid waste of different kinds coming from different sources. It relates more especially to the treatment both in an external atmosphere (aerobic phase) and in a closed medium (anaerobic phase) of organic waste and polluted materials, respectively solid or semi-solid and liquid, for directly and simultaneously producing compost, biogas and purified liquid.

2. Description of the Prior Art

The increasing volume of waste and residues of all types constitutes an increasing problem for industrialists and municipalities, considering more especially the fact that this waste generally presents great dangers for the environment and for living beings.

Very often, for liquid residues, the solution is adopted of solidifying this waste by a physico-chemical treatment giving rise to petrifaction, the hard masses obtained remaining on the treatment site or being possibly used for constructing foundation structures or different ground coverings.

According to another objective, attempts are made to make valuable use of a part at least of this waste, for example by producing heat energy or, better still, when it is a question of organic residues more or less rich in carbon and other non mineral substances, by using the known techniques of fermentation in an aerobic and/or anaerobic medium so as to obtain either composts, fertilizers and different improvements to soils or production of a gas called "biogas" rich in methane and usable as a fuel for obtaining heat or electric energy or else for manufacturing chemical products.

The invention relates to this field of making valuable use of organic waste and has essentially as aim, at one and the same time, of transforming solid organic waste into useful materials, particularly for agriculture and ensuring the treatment of liquid organic waste so as to depollute it and obtain, on the one hand, biogas and on the other purified fluids directly usable for industry or consumption.

Among the solid waste or sub-products usable as raw material in the invention, the following in particular may be mentioned: screened fractions of household waste, straw, sawdust and wood bark and ligneous materials, grape pulp, draff, bagasse, peat, herbaceous plants . . . etc.

As for liquid residues, they may in particular comprise all the concentrated refuse coming from agricultural and agricultural food production industries such for example as: sugar refineries, wine distilleries, breweries and fermentation industries, slaughter houses, and meat canning works, the dairying industries, potatostarch works, pig breeding installations . . . etc. as well of course as all the excess primary sludge and biological sludge recovered in stations for purifying urban waste water.

In what follows, the term semi-solid waste or residues will be used for designating normally solid materials but which have a water content generally between 30% and 90%, for example of the order of 45 to 80% approximately.

Fermentation in a heap, so in an aerobic medium, of different solid agricultural residues is already known for producing compost. However, these are long operations which do not in general lend themselves very well to industrialization. Moreover, producing biogas by anaerobic fermentation of semi-solid residues or sludges in digesters is known. However, this apparatus must be usually heated so as to obtain correct efficiency and the mass to be treated must be agitated and stirred; furthermore, the concentration of sludge must be made in decanters, for example lamellar decanters separate from the digester.

The essential aim of the invention is to propose a process associating the two types of aerobic and anaerobic fermentation so as to be able to simultaneously treat solid or semi-solid waste and liquid waste in order to obtain, at the outlet of a single installation, the production: of solid materials rich in fertilizing substances, biogas usable as a fuel or similar, and finally purified liquids which are immediately reusable and admissible by the environment.

Another aim is to use the heat from the aerobic fermentation so as to provide, without the need for an external supply, the ideal heat balance for the anaerobic digestion of the liquid waste or residues.

A further aim is to provide a type of digester requiring no mechanical stirring member and in which the stirring of sludge material is provided by the pressure alone of the gas generated by the fermentation in a closed medium.

Finally, yet other aims will appear from the following description, particularly the use of micro-organisms and/or enzymes, preferably fixed on certain supports, with the aim of accelerating the biological transformation process and increasing the production yields in industrial units.

SUMMARY OF THE INVENTION

To resolve the problems and reach the above mentioned aims, the invention provides a process for the simultaneous treatment of solid or semi-solid organic waste and liquid organic waste for the simultaneous production of compost and biogas, wherein the liquid organic waste is subjected to a liquid-solid separation, the liquid phase from this separation is subjected to anaerobic fermentation in at least one closed digester, the solid phase from said liquid-solid separation is mixed with said solid or semi-solid organic waste, the resulting mixture is subjected to aerobic fermentation at the periphery of said digester and in contact therewith, and sludge, clarified liquid and gas are removed from said digester whereas compost coming from the aerobic fermentation of said solid or semi-solid waste is recovered at the periphery of said digester.

The digestion sludge collected at the lower part of the closed fermenter is advantageously recycled to the phase for mixing and crushing solid carbonaceous waste, for example in the upper part of the composter, as will be seen further one, with a view to humidifying this waste up to at least 55% and also for undergoing the aerobic treatment. Furthermore, the solid sedimentary fraction of the liquid raw material to be treated (such for example as untreated waste water) is recovered and added to the mass of residues to be composted in the free atmosphere.

The aerobic treatment promotes, as is known, hydrolysis of the substrate and produces, more especially by metabolization of the polysaccharides, a great amount of energy in the form of heat which, in accordance with the invention, is used for heating the walls of the digester. This latter is then naturally kept at a temperature varying from about 35° C. to 50° C. depending on the progress of the aerobic process.

Feeding of the liquid residue into the anaerobic medium may be made from top to bottom but, more advantageously, from bottom to top in the digester. Furthermore, in the peripheral composting zone as in the heart of the digester, it is often useful to introduce an inoculum chosen from the group of yeasts, bacteria, enzymes, so as to promote the kinetics of the decomposition reactions of the substrates and to generate the formation of islets in which the microorganisms proliferate in the aerobic phase, as well as accelerating the methanogenesis phase—generally slow—in the anaerobic medium, for example by sowing appropriate bacteria such as methano sarcina, also fixed on a support.

According to a preferred embodiment, the incorporation of these inoculum takes place in a fixed medium, the fixing products being formed advantageously by fine particles, having a grain size of about 0.1 to 100 microns, of mineral products such for example as: porous glasses, silica gels, different metal oxides or else baked clays (or fireclays) which are particularly suitable. In the digester, as will be seen further on, plates, disposed on a lamellar system, are advantageously used which serve both as fixed supports for immobilizing the enzymes (for example) and as means for recovering the residual sludge from the liquid to be purified.

The invention also relates to an installation for simultaneously treating solid or semi-solid organic waste and liquid organic waste with a view to the simultaneous production of compost and biogas, comprising: means for separating the liquid organic waste into a solid phase and a liquid phase; at least one closed digester; means for introducing said liquid phase into said digester; means for mixing said solid phase with said solid or semi-solid waste; means for bringing the resulting mixture to the periphery of said digester in contact therewith; and means for discharging respectively from said digester, on the one hand, the gas which is formed therein by anaerobic fermentation and, on the other hand, the sludge which is deposited therein and finally the clarified liquid phase.

Advantageously, the digester is provided with vertical plates for fixing the bacteria and for the flow of the sludge to the bottom of the frame, these plates being for example possibly fixed to a lower grid which defines the compartment of the frame.

The storage of the biogas produced by the anaerobic fermenter may be provided in different ways. For example, the fermenter may be provided at its upper part with a gasometer or bell whose service pressure is held constant and controlled by a pressure gauge. In another variant, the installation may include a flexible gasometer, for example made from a nylon woven material impregnated with neoprene and hypalon (or other equivalent materials), installed under shelter for protection thereof.

BRIEF DESCRIPTION OF THE DRAWINGS

Numerous other features will appear in the following description, relative to non limitative embodiments illustrated by the accompanying drawings which show schematically:

FIGS. 3 and 4• representations of mounting several digesters (here two) in series and in parallel in an industrial production unit.

DESCRIPTION OF THE PREFERRED EMBODIMENTS

Figure 1:
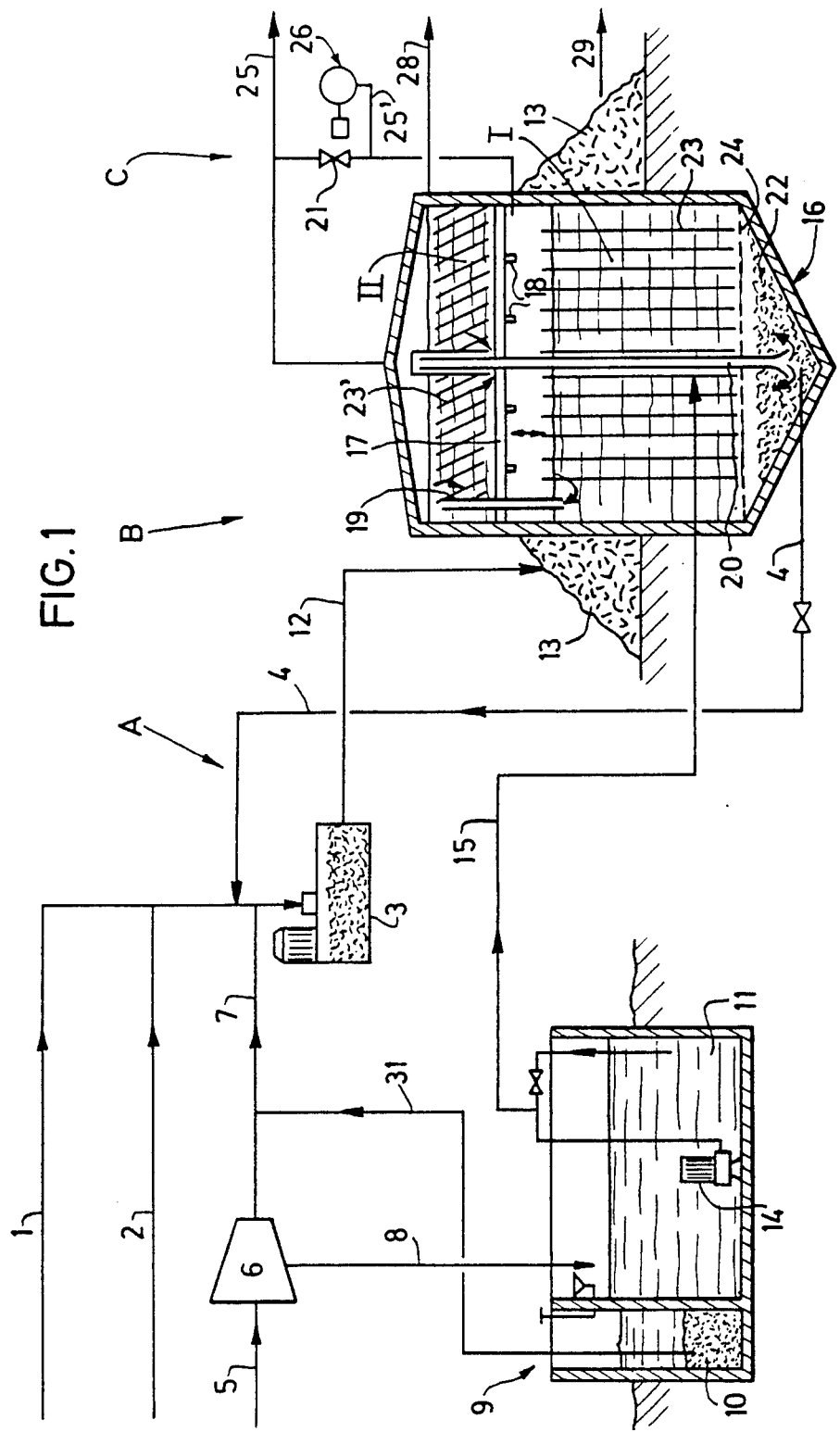
FIG. 1• a general view of an installation for implementing the process of the invention.

Such as shown in the drawings, in particular in FIG. 1, an installation for simultaneously producing compost, biogas and purified liquid in accordance with the invention comprises essentially, from left to right, an upstream part A relative to the previous treatment and to the feeding of the raw material (solid, semi-solid and liquid waste); the central part B operational for implementing the combined aerobic-anaerobic process; and the downstream zone C for recovering and possibly treating the final products obtained.

Reference will first of all be made to the upstream fraction A. The solid carbonaceous waste (wood, straw, bark, sawdust . . . etc.) is fed by transporter 1, as well as the possible nutritive additives over line 2 to a mixer-crusher 3 in which the grain size of the residues is maintained in a range from 5 to 40 mm, generally between 6 and 12 mm. Also incorporated in this solid material, through circuit 4, are the pasty sludges or residues removed from the bottom of the digester (see hereafter) so as to confer on the raw material an optimum humidity—for example, from 50 to 70% depending on the type of substrate—and providing it with the microorganism concentrates promoting the degradation. As for the liquid waste—for example here untreated waste water—it is first of all fed over line 5 to a solid-liquid separator 6, for example of the filtering drum strainer type, so as to recover over line 7 the semi-solid residues which are associated with the above-mentioned waste, the filtrate being fed over line 8 to a storage tank 9. This tank may have a new sedimentation compartment 10 from which the solid products are removed through circuit 31 as far as line 7, whereas, in the tank 11 receiving the liquid, acidification is advantageously carried out so as to facilitate the first acido-genesis phase of the anaerobic fermentation.

For the operational fermentation step B, the whole of the solid or semi-solid waste is sent over line 12 to the air fermentation heap 13, whereas the liquid mass from container 11 is fed by pump 14 and piping 15 to the closed digester 16. The aerobic degradation process of the solid or similar waste is effected, in accordance with the invention, over the whole periphery of digester 16 and it may of course be accelerated by air blowing and supplying complementary amounts of microflora so as to obtain the most appropriate C/N and C/P ratios for the production of fertilizing compost, depending on the types of raw materials used. The heat released by this fermentation, the duration of which may vary for example from about 3 to 20 days, serves for natural and permanent heating of digester 16.

As can be seen in FIGS. 1 to 4, the digester 16 is divided into two compartments I and II separated by a ceiling 17 with beams 18 and between which comunications are established by lateral tubes 19 and the central piping 20 into which is fed, through pipe 15, the liquid mass to be fermented, for example from bottom to top. According to a feature of the invention, the pressure of the gas generated in this bioreactor 16 serves for the pulsatory stirring of the mass to be treated. In fact, during this generation of gas ($CH_4$ and $CO_2$) the pressure which exists in compartment I causes the movement of the liquid from a certain level in compartment II through the pipe or pipes 19. At a given level, the opening of valve 21 for discharging the gas from compartment I gives to the liquid accumulated in compartment II the possibility of rapidly descending through the siphon 20 to the bottom of the fermenter, which causes mixing and stirring of the biomass with the liquid effluent to be treated. Between two pulses, the sedimentation of the sludge bed at I and II takes place countercurrent-wise to the effluent to be treated whereas, in the two compartments, clarification takes place. This latter is facilitated by placing in these compartments series of vertical parallel plates 23, in compartment I these plates resting on a grid 24 and small parallel sloping plates 23' in compartment II.

The variable level permanently obtained in the digester prevents the formation of a hard crust; should such a crust appear, it is broken and put back into solution through the action of the beams 18 fixed to the ceiling 17 of compartment I. The sludge 22 accumulated at the bottom of the frame is, as was mentioned above, fed back through piping 4 to the mixer-crusher 3 so as to bring the required humidity to the solid crushed waste.

In zone C the treated and generated products are discharged, namely: the recovery of the biogas at 25,25' with safety control devices 26, either towards a gasometer or directly therefrom when it is formed by a bell 27 above the digester 16 (FIG. 2); the drawing-off at 4 of the recycled sludge; and, finally, the discharge at 29 of the fermented compost for use for example as agricultural improver.

In practice, the digester is further equipped with conventional elements for this type of apparatus which are not shown for the sake of simplifying the figures, such as: inspection windows, manholes, access ladder, safety and control systems for the temperature, pressure ... etc. So as to obtain a good heat transmission coefficient, it may be provided on its external surface, except the one in contact with the compost, with material such as rock wool padding, maintenance grid and jute cloth and bituminous coated protective covering. The frame is also preferably lagged.

Figure 2:
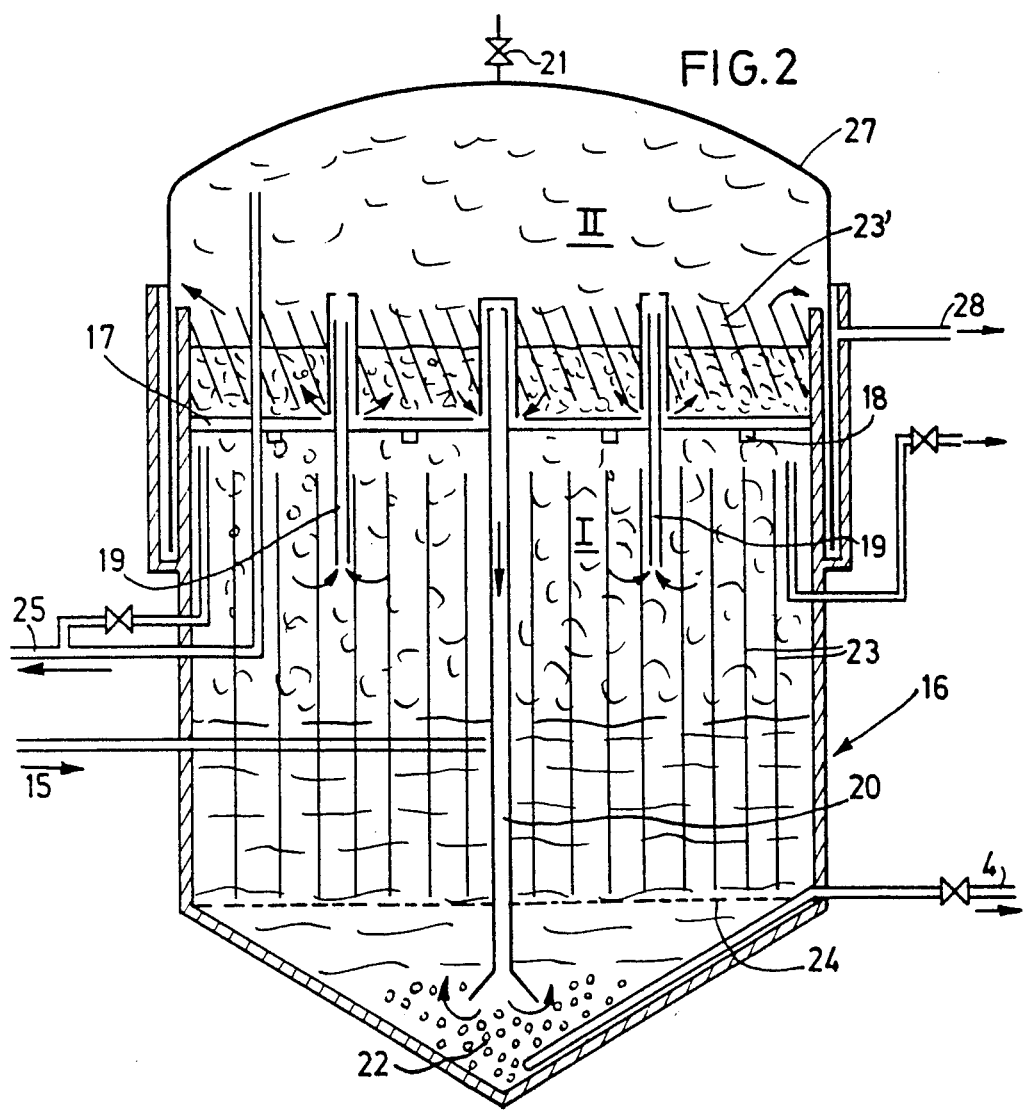
FIG. 2• a sectional simplified view of a digester of the invention fitted here with a gas bell.

For industrial production, the assemblies of aerobic fermenters or composters and anaerobic digesters in accordance with the invention may be adapted according to different arrangements, as for example in series as shown in FIG. 2 or else in parallel as shown in FIG. 4. In the first case, the liquid effluent 28' coming from the first digester is refed into the central pipe 20 of the second digester before being finally recovered at 28 whereas, in the second case, the digesters are supplied with liquid waste to be treated independently at 15 and 15'. In both cases, the biogas productions, at 25 and 25', are grouped together as well as recycling 4 of the excess sludge and the compost feed 12.

Figure 5:
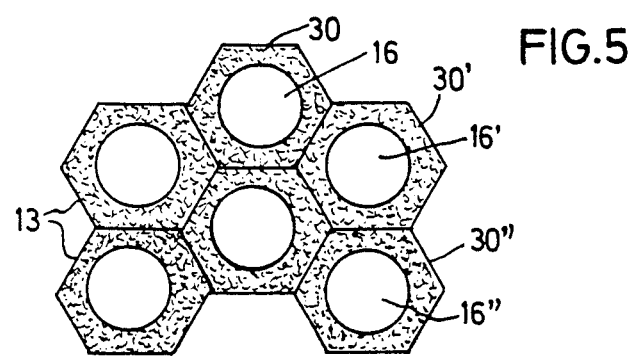
FIG. 5• the schematical illustration of a composite modular assembly: aerobic fermenters and anaerobic digesters in a honeycomb structure.

According to an interesting embodiment, the above-mentioned assemblies are designed so as to use as much as possible the heat released by the aerobic process and the heat transfers to the closed bioreactors. A particularly interesting embodiment is illustrated schematically in FIG. 5 where it can be seen that the digesters 16, 16', 16" . . . etc. are enclosed, in a honeycomb structure, between dividing walls 30, 30', 30", . . . etc., here hexagonal and made for example from concrete, of free air fermenters where the solid humidified waste is composted.

As will be understood from the foregoing description, the installation of the invention is designed for treating all types of residual organic materials (cellulose, protein, polysaccharide, lipide ... etc.), not only in the solid form but also in pasty and/or liquid form and, without departing from the scope of the invention, different variants of adaptation and appropriate dimensioning may be provided depending on the type of substrates used and the production rates of the liquid and gaseous products desired.

What is claimed is:

1. A process for the simultaneous treatment of solid or semi-solid organic waste and liquid organic waste with a view to the simultaneous production of compost and biogas, wherein said liquid organic waste is subjected to a liquid-solid separation, the liquid phase from this separation is subjected to anaerobic fermentation in at least one closed digester, the solid phase from said liquid-solid separation is mixed with said solid or semi-solid organic waste, the resulting mixture is subjected to aerobic fermentation at the periphery of said digester and in contact therewith and mud, clarified liquid and gas are respectively discharged from said digester whereas compost from the aerobic fermentation of said solid or semi-solid waste is recovered at the periphery of said digester wherein said digester is characterized by two superimposed compartments, an upper compartment at low pressure and a lower compartment at high pressure, said compartments communicating together through at least one lateral pipe and through a central siphon, means being provided for lowering the pressure of the lower compartment when the liquid reaches a predetermined level therein.

2. The process as claimed in claim 1, wherein feeding said digester with the liquid phase takes place through said siphon.

3. The process as claimed in claim 1, wherein a part of the mud separated in said digester is mixed with said organic, solid or semi-solid waste before introduction thereof into the digester.

4. The process according to one of claims 1 and 2, wherein micro-organisms fixed to supports are added to said organic waste.

5. An installation for the simultaneous treatment of solid or semi-solid organic waste and liquid waste with a view to the simultaneous production of compost and biogas, comprising: means for separating the liquid organic waste into a solid phase and a liquid phase; at least one closed digester; means for introducing said liquid phase into said digester; means for mixing said solid phase with said solid or semi-solid waste; means for bringing the resulting mixture to the periphery of said digester in contact therewith; and means for discharging respectively from said digester the gas which is formed therein by anaerobic fermentation and the sludges which are deposited therein and finally the clarified liquid phase wherein said digester is characterized by two superimposed compartments, an upper compartment at low pressure and a lower compartment at high pressure, said compartments communicating together through at least one lateral pipe and through a central siphon, means being provided for lowering the pressure of the lower compartment when the liquid reaches a predetermined level therein.

6. The installation as claimed in claim 5, further comprising means for mixing a part of the fermented sludge in the digester with said solid or semi-solid waste before introduction thereof into said digester.

7. The installation as claimed in claim 5, wherein the lower compartment of the digester comprises parallel vertical plates whereas said upper compartment comprises small inclined parallel plates.

8. The installation as claimed in claim 5, wherein said lower and upper compartments of said digester are separated by a floor below which beams project into said lower compartment.

9. The installation as claimed in claim 5, wherein feeding said digester with the liquid phase takes place through said siphon.

10. The installation as claimed in any of claims 5 to 6 or 7 to 9, further comprising a plurality of dividing walls defining a honeycomb structure and a plurality of digesters, each digester being housed in a separate cell of said structure.

* * * * *